United States Patent [19]

Buonamici et al.

[11] Patent Number: 4,847,253

[45] Date of Patent: Jul. 11, 1989

[54] ANTIPARKINSON ERGOLINE DERIVATIVES

[75] Inventors: Metilde Buonamici; Lorenzo Pegrassi; Alessandro Rossi; Sergio Mantegani, all of Milan, Italy

[73] Assignee: Farmitalia Carlo Erba, Milan, Italy

[21] Appl. No.: 273,021

[22] Filed: Nov. 18, 1988

[30] Foreign Application Priority Data

Nov. 20, 1987 [GB] United Kingdom ............... 8727236
Sep. 23, 1988 [GB] United Kingdom ............... 8822424

[51] Int. Cl.$^4$ .................. A61U 31/50; A61U 31/495
[52] U.S. Cl. ................................................. 514/253
[58] Field of Search .............................. 514/255, 253

[56] References Cited

U.S. PATENT DOCUMENTS 4,728,649 3/1988 Mantegani et al. ............... 514/253

Primary Examiner—Stanley J. Friedman
Attorney, Agent, or Firm—Oblon, Spivak, McClelland, Maier & Neustadt

[57] ABSTRACT

Compounds of the formula I

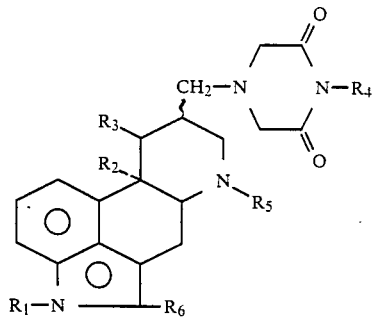

wherein $R_1$ represents a hydrogen atom or a methyl group, either $R_2$ and $R_3$ represent hydrogen atoms or together represent a chemical bond, $R_4$ represents a hydrogen atom or a $C_1$-$C_4$ alkyl group, $R_5$ represents a $C_1$-$C_4$ alkyl group or an allyl group and $R_6$ represents a hydrogen or halogen atom, and pharmaceutically acceptable salts thereof, are disclosed as being useful for the treatment of extrapyramidal syndromes such as Parkinson's disease.

9 Claims, No Drawings

ANTIPARKINSON ERGOLINE DERIVATIVES

BACKGROUND OF THE INVENTION

1. Field of the Invention

The present invention relates to a new therapeutic use of ergoline derivatives having the formula I

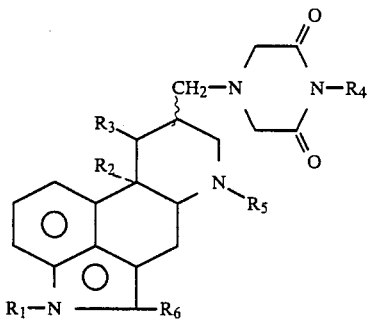

wherein $R_1$ represents a hydrogen atom or methyl group, either $R_2$ and $R_3$ represent hydrogen atoms or together represent a chemical bond, $R_4$ represents a hydrogen atom or a $C_1$–$C_4$ alkyl group, $R_5$ represents a $C_1$–$C_4$ alkyl group or an allyl group and $R_6$ represents a hydrogen or hologen atom; and pharmaceutically acceptable salts thereof.

2. Description of the Background

The compounds of the formula I and their preparation are described in U.S. Pat. No. 4,728,649, which is hereby incorporated by reference. This shows their functional anti-dopaminergic activity in normal mice. The compounds are said to have moderate to good anti-hypertensive activity and to be useful as anxiolytic and antipsychotic agents.

It is known that bromocriptine, an ergot derivative with dopaminergic activity, is an effective antiparkinson agent, but severe side effects limit the clinical usefulness of this drug. Adverse effects of bromocriptine include emesis, hypotension, cardiac arrhythmia, digital vasospasm in cold weather, conjunctival irritation, diplopia, nasal stuffiness, constipation and syndrome of bilateral red, tender edema of the lower limbs and neuroendocrine alterations. These problems are due to the fact that bromcriptine exerts its agonist effect on both central and peripheral populations of dopamine receptors.

There continues to remain a need for new and more effective antiparkison agents, which do not possess the drawbacks of the prior art compounds.

SUMMARY OF THE INVENTION

It is therefore an object of the present invention to provide a method for treating Parkinson's disease with an agent that causes fewer or reduced side effects.

This and other objects of the present invention as will hereinafter become more readily apparent have been accomplished by the discovery that compounds having the formula I

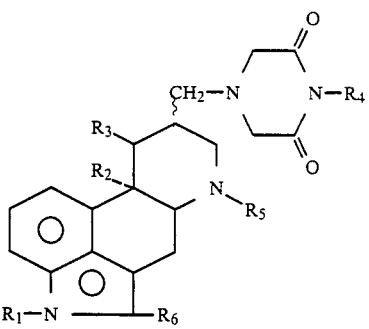

wherein $R_1$ represents a hydrogen atom or a methyl group, either $R_2$ and $R_3$ represent hydrogen atoms or together represent a chemical bond, $R_4$ represents a hydrogen atom or a $C_1$–$C_4$ alkyl group, $R_5$ represents a $C_1$–$C_4$ alkyl group or an allyl group and $R_6$ represents a hydrogen or halogen atom; and pharmaceutically acceptable salts thereof, exert a potent dopaminergic activity on central receptors when they are modified by extrapyramidal syndromes, such as in Parkinson's disease.

DETAILED DESCRIPTION OF THE PRESENT INVENTION

It has been found that the ergoline derivatives of the formula I may be unexpectedly used in the treatment of other diseases different from psychosis and anxiety. The compounds of formula I are surprisingly highly potent dopamine agonists when tested in animal experiments where central dopamine receptor supersensitivity had been induced by appropriate interventions.

Accordingly, the present invention provides the use of a compound of the formula I or a pharmaceutically acceptable salt thereof for treating extrapyramidal syndromes such as Parkinson's disease.

The ergoline derivatives of formula I and their salts induce fewer and less severe side effects than bromocriptine. They have a potent dopaminergic activity only on the central receptors when modified by extrapyramidal syndromes, such as in Parkinson's disease. They may be used alone or in association with other antiparkinson agents.

In formula I, $R_4$ is preferably methyl or hydrogen. $R_5$ may be methyl, ethyl, n-propyl, iso-propyl, n-butyl, sec-butyl, t-butyl, iso-butyl or allyl. Preferably $R_5$ is methyl. When $R_6$ is halogen, it may be fluorine, chlorine or bromine. Preferably $R_6$ is chlorine or bromine or hydrogen.

The pharmaceutically acceptable salts may be any standard acid addition salts known to those of ordinary skill in the pharmaceutical art. For example, inorganic mineral acids (HCl, HBr, etc.), lower carboxylic acid salts, and other carboxylic acids such as citric acid, oxalic acid, lactic acid, tartaric acid, etc. may be used to form the salts.

The wavy line (∿∿∿) in formula I indicates that the substituent in the 8-position may be either in the α-configuration, i.e., below the plane of the ring, or in the β-configuration, i.e., above the plane of the ring, or in both, i.e., above the plane of the ring, on in both, i.e., a mixture thereof such as a racemic mixture. Preferably the substituent in the 8-position is in the β-configuration.

Preferred ergoline derivatives for use in the present invention are identified in Table I.

TABLE I

| Laboratory Code | Chemical Name | Reference |
|---|---|---|
| FCE 23884 | 6-Methyl-9,10-didehydro-8β-(3,5-dioxo-piperazin-1-yl-methyl)-ergoline (I:$R_1=R_4=R_6=H$, $R_5=CH_3$ $R_2+R_3=$bond) | U.S. 4,728,649 Example 5 |
| FCE 23952 | 1,6-Dimethyl-8β-(3,5-dioxo-piperazin-1-yl-methyl)-ergoline (I:$R_2=R_3=R_4=R_6=H$, $R_1=R_5=CH_3$) | U.S. 4,728,649 Example 2 |
| FCE 23710 | 6-Methyl-8β-(3,5-dioxo-4-methyl-piperazin-1-yl-methyl)-ergoline (I:$R_1=R_2=R_3=R_6=H$, $R_4=R_5=CH_3$) | U.S. 4,728,649 Example 3 |
| | 6-Methyl-8β-(3,5-dioxo-piperazin-1-yl-methyl)-ergoline (I:$R_1=R_2=R_3=R_4=R_6=H$, $R_5=CH_3$) | U.S. 4,728,649 Example 1 |
| | 6-Methyl-9,10-didehydro-8α-(3,5-dioxopiperazin-1-yl-methyl)-ergoline (I:$R_1=R_4=R_6=H$, $R_5=CH_3$, $R_2+R_3=$bond) | |
| | 6-Allyl-9,10-didehydro-8β-(3,5-dioxopiperazin-1-yl-methyl)-ergolin (I:$R_1$methyl)-ergoline $R_4=R_6=H$, $R_5=$allyl, $R_2+R_3=$bond) | |
| | 6-Propyl-9,10-didehydro-8β-(3,5-dioxopiperazin-1-yl-methyl)-ergoline (I:$R_1=R_4=R_6=H$, $R_5=$propyl, $R_2+R_3=$bond) | |
| | 6-Propyl-9,10-didehydro-8α-(3,5-dioxopiperazin-1-yl-methyl)-ergoline (I:$R_1=R_4=R_6=H$, $R_5=$propyl, $R_2+R_3=$bond) | |
| | 2-Chloro-6-methyl-9,10-didehydro-8β-(3,5-dioxopiperazin-1-yl-methyl)-ergoline (I:$R_1=R_4=H$, $R_5=CH_3$, $R_6=Cl$, $R_2+R_3=$bond) | |
| | 2-Bromo-9,10-didehydro-8β-(3,5-dioxopiperazin-1-yl-methyl)-ergoline (I:$R_1=R_4=H$, $R_5=CH_3$, $R_6=Br$, $R_2+R_3=$bond) | |

The ergoline derivatives of formula I and their pharmaceutically acceptable salts are useful in the therapy of extrapyramidal symptomes such as Parkinson's disease. Thus, they may be used for the treatment of Parkinson's disease and for the improvement of effectiveness with control of side-effects when used in association with other antiparkinson agents.

Accordingly, the compounds of formula I and their pharmaceutically acceptable salts can be used to treat extrapyramidal symptoms such as Parkisonism by administering to a patient in need of said treatment a therapeutically effective amount of one or a combination of said compounds or salts. Morbus Parkison can therefore be treated by use of a compound of formula I or a pharmaceutically acceptable salt thereof.

Biological Tests

The anti-dopaminergic activity in normal mice of the ergoline derivatives according to the invention was assessed by the antagonism to apomorphine-induced climbing (Protais, P. et al., Psychopharmacology, 50, 1, 1976).

The obtained results are reported in Table II.

TABLE II

| Compound | Apomorphine antagonism (ED$_{50}$, mg/kg p.o.) |
|---|---|
| FCE 23884 | 0.5 |
| FCE 23952 | 0.9 |
| FCE 23710 | 2.2 |
| Bromocriptine | Inactive at 10 mg/kg |

Effect on Turning Behavior in 6-OHDA Lesioned Rats

The profile of dopamine agonists of the compound of the formula I was preliminary discovered by an induction of contralateral turning in rats with unilateral 6-hydroxy dopamine-induced lesions of the dopaminergic nigrostriatal pathway (according to the principles of U. Ungerstedt et al., Brain Research 24·(1970); p. 485).

Methods

Male (ICR) Wistar rats (290–310 g) anaesthetized i.p. with 50 mg/kg pentobarbital sodium were placed in a Stoelting stereotaxis frame and unilaterally injected with 6-hydroxy-dopamine (6-OHDA) in substantia nigra, pars compacta (8 μg of free base in 4 μl of saline kept ice cold with 0.2% ascorbic acid at the rate of 1 μl/min.). The neurotoxin was injected via a 10 μl Hamilton syringe under the following coordinates: A, 3.7 mm anterior to interaural line; V. 2.2 mm dorsal to interaural line; L, 2.2 mm from midline, according to Paxinos and Watson (The rat brain in stereotaxic coordinates. Academic Press, Sydney, Australia, 1982).

The needle was left in place 5 minutes further before being slowly withdrawn.

Following recovery from anaesthesia, rats were housed in a cage and given access to food and water ad libitum. After a 3 week recovery, rats were injected with apomorphine (0.5 mg/kg s.c.) and immediately put in automated rotometer bowls with a printing unit for 3 hours.

Only rats showing contralateral turning behavior totalling at least 250 complete turns within the control time, were used for the test with the compounds.

The test compounds were injected subcutaneously and rotational behavior scored each time for six hours. All tested compounds were administered in a fixed volume (2 ml/kg body weight).

The obtained results are reported in Table III.

TABLE III

Effect of the Tested Compounds on Turning Behavior In 6-OHDA Lesioned Rats

| Compounds | mg/kg s.c. | Turning rats/ Treated rats | No. of contralateral turns (X) in turning rats |
|---|---|---|---|
| FCE 23884 | 1.0 | 5/5 | 2146 |
| | 0.5 | 10/10 | 2591.7 |
| | 0.1 | 9/10 | 1317.5 |
| FCE 23952 | 1.0 | 4/4 | 710.5 |
| FCE 23710 | 1.0 | 4/4 | 1829.2 |
| Bromocriptine | 1 | 6/9 | 1922.3 |

The orientative acute toxicity of the compounds I in rats is higher than 300 mg/kg p.o.

The compounds are therefore indicated for use as antiparkison agents.

The amount of active compound for this indication will, of course, be dependent on the subject being treated, the severity of the application, the manner of administration and the judgment of the prescribing physician.

However, an effective dosage is in the range of about 0.01 to about 5 mg, preferably about 0.1 to about 3 mg, conveniently given in divided doses 1 to 5 times a day in unit dosage form containing from about 0.01 to about 2 mg of the compound or in sustained release form.

Administration and Compositions

Administration of the active compound and salts described herein can be via any of the accepted modes of administration for antiparkison agents.

The routes of administration include parenteral, oral, buccal, peroral, transdermal, intranasal or other suitable routes. Depending on the intended route of administration, such compositions may be formulated in a conventional manner or in other pharmaceutical systems for delivery of the drug in a rate and extent needed for the intent therapeutical use.

The composition will include a conventional pharmaceutical carrier or excipient and an active compound of formula I or the pharmaceutically acceptable salts thereof and, in addition, may include other medicinal agents, pharmaceutical agents, carriers, adjuvants, etc.

For a solid composition, conventional nontoxic solid carriers including, for example, pharmaceutical grades if mannitol, lactose, starch, magnesium, stearate, sodium saccharin, talcum, cellulose, glucose, sucrose, magnesium carbonate and the like may be used. Liquid pharmaceutically administerable compositions can, for example, be prepared by dissolving, dispersing, etc., an active compound as defined above and optionally a pharmaceutical adjuvant in a carrier, such as, for example, water, saline, aqueous dextrose, glycerol, ethanol and the like, to thereby form a solution or suspension.

The compound coded FCE 23884 is the preferred compound.

The following examples still further illustrate the invention without limiting it.

EXAMPLE 1

Locomotor Activity in Reserpine-Treated Mice

Method

Male mice, (22-25 g) of the Crl:CD$^R$ -1 (ICR) BR strain, were used. Injection volume for drugs was 0.5 ml/100 g body weight. Locomotor activity in mice was examined from 5 up to 90 min. by use of two "Columbus activity Meters" placing 5 animals per cage after each treatment. Comparison was made with reserpine treated animals (5 mg/kg i.p.) receiving saline (controls).

Groups of five mice were used each time. Eighteen hours reserpine pretreated mice were subcataneously injected with the test compound or apomorphine or saline.

Five minutes later, the animals were tested for locomotor activity according D. Hinzen et al., European Journal of Pharmacology 131 (1986) 75-86.

Results (see Table IV)

As shown in Table IV, FCE 23884 at a dose of 1 mg/kg s.c. elicits locomotor activity as does apomorphine—the classical dopaminergic agonist—in akinetic reserpinized mice.

TABLE IV

| Locomotor Activity in Reserpine-Treated Mice (5 mg/kg i.p.) | | | |
|---|---|---|---|
| Compound | Dosage mg/kg s.c. | Number of animals | No. of counts in 85 min. |
| Reserpine + saline | — | 10 | 15 |

TABLE IV-continued

| Locomotor Activity in Reserpine-Treated Mice (5 mg/kg i.p.) | | | |
|---|---|---|---|
| Compound | Dosage mg/kg s.c. | Number of animals | No. of counts in 85 min. |
| Reserpine + apomorphine | 0.05 | 10 | 413 |
| Reserpine + FCE 23884 | 1.0 | 15 | 625 |

EXAMPLE 2

MPTP-Induced Parkinsonism in Monkey Model

In nonhuman primates MPTP (1-methyl-4-phenyl-1,2,3,6-tetrahydropyridine) selectively destroys dopaminergic neurons in the substantia nigra pars compacta as has been shown in different primate species (1) (2) including the common marmoset and cynomolgus.

Repeated administration of MPTP produces varying degrees of akinesia or bradykinesia accompanied by rigidity of limbs, loss of vocalization and postural tremor.

The early motor deficits produced by MPTP mimic the major symptoms occurring in human Parkinson's disease and all these behavioral effects can be reversed by L-DOPA plus carbidopa or by some other dopaminergic drugs.

Marmosets and cynomolgus were employed in these experiments. Each animal was administered a variable dosage regime showing them to have an individual susceptibility to MPTP according to Jenner et al. (3).

For the marmoset the cumulative dose was between 11-29 mg/kg i.p. over time courses of 4-10 days for three marmosets and 10-12 mg/kg i.p. for two cynomolgus in 4 days. All the monkeys were severely affected, completely akinetic and rigid with loss of vocalization, and blink reflex, with some postural tremor and were rendered unable to eat by themselves. After two or three days of wash-out to avoid the acute effect of MPTP administration, compound FCE 23884 was injected subcutaneously once a day starting from the dose 0.1 mg/kg up to 2 mg/kg. Reversal of akinesia in a dose-dependent fashion was observed.

Saline was administered in alternate fashion every three treatements to avoid the normal described improvement after the suspension of MPTP administration.

Depending on the dose, reversal of akinesia was observed starting from 30 minutes for the lowest dose (0.1 mg/kg s.c.) to 5 minutes for the highest dose (2 mg/kg s.c.).

The same compound, injected subcutaneously to non-MPTP treated monkeys, showed a sedative effect in a dose-dependent fashion, like an antidopaminergic compound reproducing the same behavioral patterns already seen in normal rats, while it showed a dopaminergic effect in lesioned animals.

From the results obtained, compound FCE 23884 is considered to be a dopaminergic agent in the MPTP treated monkeys and an antidopaminergic in non MPTP-treated monkeys.

(1) Langston J. W. et al., Brain Res. 292:390-394, 1984.

(2) Burns R. S. et al., Pro. Natl. Acad. Sci. USA 80.:4546-4550, 1983.

(3) Jenner P. et al., J. Neuronal Trans. Suppl. 20:11-39, 1986.

What is claimed as new and desired to be secured by Letters Patent of the United States is:

1. A method of treating an extrapyramidal syndrome in a patient in need thereof, which comprises administering to said patient an effective amount of a compound of the formula I

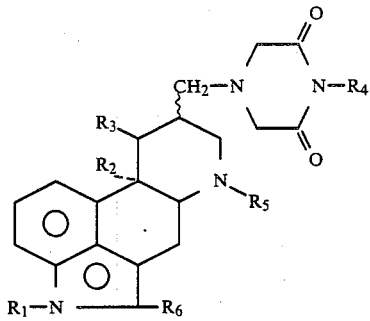

wherein $R_1$ represents a hydrogen atom or methyl group, either $R_2$ and $R_3$ represent hydrogen atoms or together represent a chemical bond, $R_4$ represents a hydrogen atom or a $C_1$-$C_4$ alkyl group, $R_5$ represents a $C_1$-$C_4$ alkyl group or an allyl group and $R_6$ represents a hydrogen or halogen atom; or a pharmaceutically acceptable salt thereof.

2. The method according to claim 1, wherein said extrapyramidal syndrome is Parkison's disease.

3. The method according to claim 1, wherein $R_4$ is methyl.

4. The method according to claim 1, wherein $R_5$ is methyl.

5. The method according to claim 1, wherein the substituent in the 8-position is in the $\beta$-configuration.

6. The method according to claim 1, wherein $R_6$ is chlorine, bromine or hydrogen.

7. The method according to claim 1, wherein the compound of formula I is 6-methyl-9,10-didehydro-8$\beta$-(3,5-dioxo-piperazin-1-yl-methyl)ergoline.

8. The method according to claim 1, wherein said effective amount is in the range of about 0.01 to about 5 mg, per dose.

9. The method according to claim 1, wherein said compound is administered to said patient 1 to 5 times per day in unit dosage form containing from about 0.01 to about 2 mg of said compound.

* * * * *